US008431336B2

(12) United States Patent
Lee et al.

(10) Patent No.: US 8,431,336 B2
(45) Date of Patent: *Apr. 30, 2013

(54) BINDING INTERACTIONS IN DIPSTICK ASSAYS

(75) Inventors: Helen Lee, Cambridge (GB); Magda Anastassova Dineva, Cambridge (GB); Hsiang Yun Hu, Union City, CA (US)

(73) Assignee: Diagnostics for the Real World, Ltd., Sunnyvale, CA (US)

( * ) Notice: Subject to any disclaimer, the term of this patent is extended or adjusted under 35 U.S.C. 154(b) by 418 days.

This patent is subject to a terminal disclaimer.

(21) Appl. No.: 10/332,142

(22) PCT Filed: Jul. 6, 2001

(86) PCT No.: PCT/GB01/03039
§ 371 (c)(1),
(2), (4) Date: Apr. 7, 2003

(87) PCT Pub. No.: WO02/04671
PCT Pub. Date: Jan. 17, 2002

(65) Prior Publication Data
US 2004/0072176 A1    Apr. 15, 2004

(30) Foreign Application Priority Data
Jul. 7, 2000  (GB) .................................. 0016836.9

(51) Int. Cl.
*C12Q 1/68*     (2006.01)
*C07H 21/02*    (2006.01)
*C07H 21/04*    (2006.01)
*C12P 19/34*    (2006.01)

(52) U.S. Cl.
USPC ........................... 435/6.1; 536/23.1; 536/24.3

(58) Field of Classification Search ........................ None
See application file for complete search history.

(56) References Cited

U.S. PATENT DOCUMENTS

| 4,751,177 | A |   | 6/1988  | Stabinsky |           |
|-----------|---|---|---------|-----------|-----------|
| 4,822,731 | A |   | 4/1989  | Watson et al. ..................... 435/6 |
| 4,868,105 | A |   | 9/1989  | Urdea et al. ....................... 435/6 |
| 4,950,744 | A |   | 8/1990  | Dattagupta et al. ............. 536/27 |
| 5,210,015 | A |   | 5/1993  | Gelfand et al. |
| 5,283,174 | A |   | 2/1994  | Arnold et al. ..................... 435/6 |
| 5,310,650 | A | * | 5/1994  | McMahon et al. ................ 435/6 |
| 5,310,885 | A | * | 5/1994  | Maier et al. .................... 530/413 |
| 5,317,098 | A |   | 5/1994  | Shizuya et al. ............... 536/23.1 |
| 5,328,825 | A | * | 7/1994  | Warren et al. ..................... 435/6 |
| 5,436,327 | A |   | 7/1995  | Southern et al. ........... 536/25.34 |
| 5,510,084 | A |   | 4/1996  | Cros et al. ..................... 422/104 |
| 5,573,913 | A | * | 11/1996 | Rosemeyer et al. ............. 435/6 |
| 5,695,926 | A |   | 12/1997 | Cros et al. ...................... 435/5 |
| 5,712,383 | A |   | 1/1998  | Sheridan et al. ............. 536/24.3 |
| 5,738,984 | A | * | 4/1998  | Shoseyov .......................... 435/4 |
| 5,747,248 | A |   | 5/1998  | Collins |
| 5,789,167 | A | * | 8/1998  | Konrad ............................. 435/6 |
| 5,849,544 | A | * | 12/1998 | Harris et al. .................. 435/91.2 |
| 5,849,878 | A | * | 12/1998 | Cantor et al. ............... 530/391.9 |
| 5,874,216 | A | * | 2/1999  | Mapes .......................... 435/6.11 |
| 5,925,517 | A | * | 7/1999  | Tyagi et al. ....................... 435/6 |
| 5,976,789 | A |   | 11/1999 | Allibert et al. .................... 435/6 |
| 6,214,549 | B1|   | 4/2001  | Weindel et al. |
| 6,537,749 | B2| * | 3/2003  | Kuimelis et al. ................. 435/6 |
| 7,186,508 | B2|   | 3/2007  | Lee et al. ......................... 435/6 |
| 7,192,701 | B2|   | 3/2007  | Lee et al. ......................... 435/6 |
| 2002/0012913 | A1 |   | 1/2002 | Gunderson et al. |
| 2004/0014094 | A1 |   | 1/2004 | Lee et al. |
| 2004/0048395 | A1 |   | 3/2004 | Lee et al. |
| 2004/0072176 | A1 |   | 4/2004 | Lee et al. |
| 2005/0084862 | A1 |   | 4/2005 | Lee et al. |
| 2006/0149164 | A1 |   | 7/2006 | Lee et al. |
| 2007/0190548 | A1 |   | 8/2007 | Lee et al. |
| 2008/0160516 | A1 |   | 7/2008 | Lee et al. |

FOREIGN PATENT DOCUMENTS

| AU | 659866 B2    | 6/1995  |
| DE | 19901761     | 7/1999  |
| EP | 0152886      | 2/1985  |
| EP | 0 163 220 A2 | 12/1985 |
| EP | 0 198 662 A1 | 10/1986 |
| EP | 0387696      | 3/1990  |

(Continued)

OTHER PUBLICATIONS

Weir, S.C. et al., "Detection of *Legionella* by PCR in Respiratory Specimens Using a Commercially Available Kit", Am. J. Clin. Pathol., vol. 110, pp. 295-300 (1998).*
Kessler, C., "Non-radioactive analysis of molecules", J. Biotechnol., vol. 35, pp. 165-189 (1994).*
Agrawal, S. et al., "Efficient methods for attaching non-radioactive labels to the 5' ends of synthetic oligodeoxyribonucleotides", Nucl. Acids Res., vol. 14, pp. 6227-6242 (1986).*
Hendrickson, E.R. et al., Nucl. Acids Res., vol. 23, pp. 522-529 (1995).*
Gravitt et al., Journal of Clinical Microbiology 36(10): 3020-3027 (1998).
Ju et al., Nucleic Acids Research 24(6): 1144-1148 (1996).
O'Brien et al., AJPH 78(12): 1583-1584 (1998).
Reinhartz et al., Gene 136: 221-226 (1993).
Senior et al., Biochemistry 27: 3879-3885 (1988).

(Continued)

*Primary Examiner* — Teresa E Strzelecka
(74) *Attorney, Agent, or Firm* — Seed IP Law Group PLLC

(57) ABSTRACT

Use of dipsticks to test for the presence of target nucleic acid in a sample solution is described. The dipsticks comprise a contact end for contacting the sample solution and a capture zone, remote from the contact end, to which a capture probe is immobilized. The capture probe is capable of hybridising to the target nucleic acid. The sample solution is contacted with the contact end of the dipstick and travels by capillary action to the capture zone. If target nucleic acid is present in the sample solution it is captured and can be detected at the capture zone. The capture probe is immobilized to the capture zone by a spacer. Use of the spacer increases the stability of the interaction between the capture probe and the target nucleic acid and thus improves the sensitivity of target nucleic acid detection. Detection probes with spacers are also described.

7 Claims, 7 Drawing Sheets

FOREIGN PATENT DOCUMENTS

| | | |
|---|---|---|
| EP | 0420260 | 9/1990 |
| EP | 0905258 | 11/1993 |
| WO | WO89/04375 | 5/1989 |
| WO | WO90/01564 | 2/1990 |
| WO | 91/00288 A1 | 1/1991 |
| WO | WO 91/08307 | 6/1991 |
| WO | WO93/02213 | 2/1993 |
| WO | WO93/13224 | 7/1993 |
| WO | WO94/00600 | 1/1994 |
| WO | 94/06810 A1 | 3/1994 |
| WO | WO94/06940 | 3/1994 |
| WO | 94/23299 A1 | 10/1994 |
| WO | 94/29696 A1 | 12/1994 |
| WO | 95/05391 A1 | 2/1995 |
| WO | 95/16055 A1 | 6/1995 |
| WO | WO95/27081 | 10/1995 |
| WO | WO96/35696 | 11/1996 |
| WO | WO98/15564 | 4/1998 |
| WO | 00/34457 A1 | 6/2000 |
| WO | WO00/61806 | 10/2000 |

OTHER PUBLICATIONS

Winter et al., Nucleosides & Nucleotides 18(3): 411-423 (1999).
Groody, Molecular Biotechnology 6: 323-327 (1996).
Dahl et al., Nucleic Acids Research 15(4): 17291743 (19870.
Yuriev et al., "Effects of 5-[S-(2,4-dinitrophenyl)-thio]-2'-deoxyuridine analog incorporation on the structure and stability of DNA hybrids: implications for the design of nucleic acid probes," *J. Mol. Recognit.* 12:337-345, 1999.

\* cited by examiner

| Detection Probe Name | Structure |
|---|---|
| dp-B⁵' |  |
| dp-(N)ₓ-B⁵' |  |
| dp-(S)ᵧ-B⁵' |  |
| ³'B-dp |  |
| dp-(dS)₆-B⁵' |  |
| dp-(SC₃)₆-B⁵' |  |
| dp-SN₃SN₃S-B⁵' |  |

Figure 14

| No EB* | $5 \times 10^6$ | $10^6$ | $5 \times 10^5$ | $2.5 \times 10^5$ | $10^5$ | $7.5 \times 10^4$ | $5 \times 10^4$ | $2.5 \times 10^4$ | $10^4$ | $5 \times 10^3$ | NC** |
|---|---|---|---|---|---|---|---|---|---|---|---|
| Time first signal | 2.20' | 2.50' | 3.30' | 4.30' | 5.35' | 8.10' | 8.45' | 14.05' | 24' | - | - |
| Signal at 10' | 4 | 3 | 2.5 | 2 | 1.5 | 1 | 1 | 0.5 | 0 | 0 | 0 |
| Signal at 20' | 5 | 4 | 3.5 | 3 | 2.5 | 2 | 1.5 | 1 | 0.25 | 0 | 0 |
| Signal at 30' | 5 | 4.5 | 4.0 | 3.5 | 3.0 | 2.5 | 2.0 | 1.5 | 1.0 | 0 | 0 |
| Signal at 1 h | 5 | 4.5 | 4.0 | 3.5 | 3.0 | 2.5 | 2.0 | 1.0 | 0.5 | 0 | 0 |

*Number elementary bodies (EB) of *Chlamydia trachomatis*
**NC: Negative control

SEQUENCE LISTING

<160> NUMBER OF SEQ ID NOS: 17

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tgcaactctt ggtggtagac tttgc                                              25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcgcacagac gatctatttt ttgca                                              25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgggcgattt gccttaaccc cacca                                              25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccaagcttaa gacttcagag gagcg                                              25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
catgcgtttc caataggatt cttgg                                              25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
cacagtcaga aattggagtg ctggc                                          25
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 7

```
cttgctgctc gaacttgttt agtac                                          25
```

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 8

```
agaagtcttg gcagaggaaa ctttt                                          25
```

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 9

```
ctagaattag attatgattt aaaaggg                                        27
```

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 10

```
ttcatatcca aggacaatag accaa                                          25
```

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 11

```
tgatctacaa gtatgtttgt tgagt                                          25
```

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 12

```
tgcataataa cttcgaataa ggagaag                                        27
```

```
<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tccctcgtga tataacctat ccg                                                 23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
caggttgtta acaggatagc acgc                                                24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctcgttccga aatagaaaat cgca                                                24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggtaaagctc tgatatttga agac                                                24

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctgaggcagc ttgctaatta tgagt                                               25
```

BINDING INTERACTIONS IN DIPSTICK ASSAYS

This application is a 371 of PCT/GB01/03039 on Jul. 6, 2001, which is hereby incorporated by reference.

The present invention relates to enhanced nucleic acid detection by dipsticks. Dipsticks of the invention are used to detect the presence of a target nucleic acid in a sample solution, for example to identify whether a patient is infected with a disease causing microorganism such as *Chlamydia trachomatis*.

Some conventional tests for detecting the presence of a target nucleic acid in a sample solution rely on amplification of the target nucleic acid using the polymerase chain reaction (PCR). Whilst this reaction allows detection of small quantities of target nucleic acid, it can take several hours before a result is obtained. This can be a significant disadvantage because it is often desired to obtain the result as quickly as possible, for example, to keep patient waiting times to a minimum. Further disadvantages of such methods are the requirement for expensive specialist equipment to perform the reaction and the relatively high cost of the reagents.

In contrast, dipsticks detect unamplified target nucleic acid without the requirement for any specialist equipment and the results can be obtained much more rapidly than PCR-based methods. Patients can then be treated in the same visit. This is particularly advantageous where the patient is unlikely to, or cannot, return at a later date.

In a typical conventional dipstick described in U.S. Pat. No. 5,310,650, a single stranded DNA capture probe is immobilised on a nitrocellulose filter at a capture zone remote from one end of the filter (the contact end). Part of the sequence of the capture probe is complementary to the sequence of a first region of the target nucleic acid to be detected. A labelled single stranded DNA detection probe is immobilised on the nitrocellulose filter at a probe zone located between the capture zone and the contact end of the filter. The detection probe has sequence complementary to the sequence of a second region (distinct from the first region) of the target nucleic acid.

To detect target DNA in a sample solution thought to contain target DNA, the contact end of the nitrocellulose filter is contacted with the sample solution. The sample solution wicks up the filter by capillary action and passes the probe zone and the capture zone. As the sample solution passes the probe zone, it mobilises the detection probe and causes it to rise with the sample solution towards the capture zone. Mobilised detection probe can then hybridise to the second region of any target DNA present in the sample solution.

When the hybridised detection probe and target DNA arrive at the capture zone, the first region of the target DNA can hybridise to the immobilised capture probe. A ternary complex is thereby formed between the target nucleic acid, the capture probe and the labelled detection probe. Presence of label at the capture zone, therefore, indicates that target DNA is present in the sample solution.

With a second type of conventional dipstick, the labelled DNA detection probe is not immobilised on the nitrocellulose filter. Instead the detection probe is added to the sample solution under conditions allowing hybridisation of the detection probe to any target nucleic acid in the sample solution. The contact end of the nitrocellulose filter is then contacted with the sample solution and as the sample solution wicks up the dipstick, target nucleic acid which is hybridised to the detection probe is captured at the capture zone by the capture probe.

It has been found, however, that the sensitivity of nucleic acid detection by conventional dipsticks can be low. If the target nucleic acid is double stranded, the sensitivity of dipstick detection can be particularly low. Consequently, the presence of target nucleic acid in a sample solution can sometimes be undetected. It is desired, therefore, to improve the sensitivity of target nucleic acid detection by dipsticks.

According to a first aspect of the invention there is provided a dipstick for testing for the presence of target nucleic acid in a sample solution which comprises:

a chromatographic strip having a contact end for contacting the sample solution; and a capture probe immobilised at a capture zone of the chromatographic strip remote from the contact end, the capture probe being capable of hybridising to the target nucleic acid or to a hook capture probe bound to the target nucleic acid, wherein the capture probe is linked to a capture probe spacer and the capture probe spacer is linked to the capture zone, thereby immobilising the capture probe at the capture zone and spacing the capture probe from the capture zone.

The term 'chromatographic strip' is used herein to mean any porous strip of material capable of transporting a solution by capillarity.

The capture probe spacer may comprise any component which spaces the capture probe from the capture zone without preventing the capture probe from being able to hybridise to the target nucleic acid or hook capture probe. Preferably the capture probe spacer comprises a biopolymer.

The capture probe spacer may comprise a protein. The term 'protein' is used herein to mean any compound comprising one or more amino acid residues. Examples of preferred proteins are naturally occurring proteins, preferably bovine serum albumin (BSA), thyroglobulin, or derivatives thereof. Derivatives include proteins which differ from BSA or thyroglobulin by amino acid substitution, addition, or deletion, or by post-translational modification.

In order to link the capture probe to the protein spacer it will generally be necessary to functionalise the capture probe. This can be done by the use of a modifier comprising a first reactive group capable of reacting with the capture probe and a second reactive group capable of reacting with the protein. A suitable modifier comprises a phosphoramidite group and a primary amino group (or a protected primary amino group which is deprotected before use). The phosphoramidite group is capable of reacting with a hydroxyl group (usually the 5'-OH or the 3'-OH of the capture probe when the capture probe is a nucleic acid) and the primary amino group is capable of reacting with a carboxyl group of the protein. An example of a suitable modifier is 6-(Trifluoroacetylamino) hexyl-(2-cyanoethyl)-(N,N-diisopropyl)-phosphoramidite (C6-TFA). Other suitable modifiers will be known to those of ordinary skill in the art.

Once the modifier has reacted with the capture probe and the protein to link the capture probe to the protein the reacted modifier is termed herein a 'linker'.

Preferably the protein is adsorbed directly to the capture zone.

In conventional dipsticks, the detection probe or capture probe is immobilised to the dipstick by covalent attachment, adsorption, use of heat or by UV cross-linking. However, it has been found that proteins may be more readily and efficiently immobilised to the dipstick than the capture probe. Consequently, direct adsorption of the protein to the capture zone is a more convenient and more efficient means of immobilising the capture probe to the dipstick than conventional immobilisation.

The capture probe spacer may comprise a non protein. In a preferred arrangement, the capture probe spacer comprises a protein and a non protein, the capture probe being coupled to the non protein and the non protein being coupled to the protein thereby spacing the capture probe from the protein.

In order to link the non protein to the protein it will generally be necessary to use a modifier comprising a first reactive group capable of reacting with the non protein and a second reactive group capable of reacting with the protein.

A suitable modifier for use with non proteins which comprise a hydroxyl group is 6-(Trifluoroacetylamino)hexyl-(2-cyanoethyl)-(N,N-diisopropyl)-phosphoramidite (C6-TFA). Other suitable modifiers will be known to those of ordinary skill in the art.

Once the modifier has reacted with the non protein and the protein to link the non protein to the protein the reacted modifier is termed herein a 'linker'.

Examples of suitable non protein spacer components include 1',2'-Dideoxyribose phosphate (dS), 3-Hydroxypropyl phosphate ($S_{C3}$), and Hexaethyleneglycol phosphate (S). The chemical structures of these compounds are shown in FIG. 1.

Preferably, however, the non protein comprises a nucleobase is capable of forming a stacking interaction with a base pair formed when the capture probe has hybridised to the target nucleic acid or hook capture probe. More preferably the non protein comprises a nucleotide. Most preferably the non protein consists only of one or more nucleotides.

Preferably the non protein is at least the length of three nucleotide monomers. The length of one nucleotide monomer (N) is approximately equal to the length of one 1',2'-Dideoxyribose phosphate (dS) or one 3-Hydroxypropyl phosphate ($S_{C3}$). Three nucleotide monomers are approximately equal to the length of one Hexaethyleneglycol phosphate (S).

The capture probe spacer may be linked to any part of the capture probe which does not prevent the capture probe from hybridising to the target nucleic acid or the hook capture probe. If the capture probe spacer is linked to a part of the capture probe between the ends of the capture probe, one or both ends of the capture probe may be coupled to one or more nucleotides, preferably at least three nucleotides, which do not hybridise to the target nucleic acid when the capture probe has hybridised to the target nucleic acid, or which do not hybridise to the hook capture probe when the capture probe has hybridised to the hook capture probe.

Preferably the capture probe spacer is linked to one end of the capture probe. If the capture probe spacer is linked to one end of the capture probe, the end of the capture probe not linked to the capture probe spacer may be coupled to one or more nucleotides, preferably at least three nucleotides, which do not hybridise to the target nucleic acid when the is capture probe has hybridised to the target nucleic acid, or which do not hybridise to the hook capture probe when the capture probe has hybridised to the hook capture probe.

The hook capture probe may comprise a first region capable of hybridising to the target nucleic acid and a second region capable of hybridising to the capture probe thereby enabling indirect binding of the capture probe to the target nucleic acid. The hook capture probe may comprise at least one nucleic acid or nucleic acid analogue.

Dipsticks of the first aspect of the invention may be used in methods for testing for the presence of target nucleic acid in a sample solution in which a detection probe capable of hybridising to the target nucleic acid is incubated with the sample solution under conditions for hybridisation of the detection probe to target nucleic acid. The contact end of the dipstick is contacted with the sample solution allowing sample solution to move up the dipstick by capillary action. Target nucleic acid hybridised to the detection probe in the sample solution can then be captured by the capture probe at the capture zone. The presence of target nucleic acid in the sample solution is then indicated by the presence of the detection probe at the capture zone.

Accordingly the invention also provides a kit for testing for the presence of target nucleic acid in a sample solution which comprises:

a dipstick of the first aspect of the invention; and a detection probe capable of hybridising to the target nucleic acid thereby allowing detection of target nucleic acid utilising the detection probe.

Instead of incubating the detection probe with the sample solution, the detection probe may be releasably immobilised to the dipstick, for example at a probe zone between the contact end and the capture zone of the chromatographic strip. To test for the presence of target nucleic acid in a sample solution, the contact end of the dipstick can be contacted with the sample solution so that sample solution wicks up the dipstick by capillary action. As the sample solution passes the probe zone of the dipstick it mobilises the detection probe so that the detection probe can hybridise to target nucleic acid in the sample solution and move with the target nucleic acid to the capture zone. Target nucleic acid hybridised to the detection probe is captured by the capture probe as the sample solution passes the capture zone. The presence of target nucleic acid in the sample solution is then indicated by the presence of the detection probe at the capture zone.

The detection probe may be coupled to a label thereby allowing direct detection of target nucleic acid at the capture zone. Alternatively the detection probe may be coupled to a detection ligand allowing indirect detection of target nucleic acid using a detection ligand binding moiety. The label or the detection ligand may be linked to a detection probe spacer which is linked to the detection probe, thereby coupling the label or the detection ligand to the detection probe and spacing the label or the detection ligand from the detection probe.

According to a second aspect of the invention there is provided a dipstick for testing for the presence of target nucleic acid in a sample solution which comprises:

a chromatographic strip having a contact end for contacting the sample solution;

a capture moiety, immobilised at a capture zone remote from the contact end, the capture moiety being capable of binding directly or indirectly to the target nucleic acid; and a detection probe, releasably immobilised at a probe zone located between the contact end and the capture zone, the detection probe being capable of hybridising to the target nucleic acid and the detection probe being coupled to a label allowing direct detection of the detection probe, or the detection probe being coupled to a detection ligand allowing indirect detection of the detection probe;

wherein the label or the detection ligand is linked to a detection probe spacer and the detection probe spacer is linked to the detection probe thereby coupling the label or the detection ligand to the detection probe and spacing the label or the detection ligand from the detection probe.

The detection probe spacer may comprise any component which spaces the detection probe from the label or ligand without preventing the detection probe from being able to hybridise to the target nucleic acid. Preferably the detection probe spacer comprises a biopolymer.

The detection probe spacer may comprise a protein. The term 'protein' is used herein to mean any compound comprising one or more amino acid residues. Examples of preferred proteins are naturally occurring proteins such as bovine serum albumin (BSA), thyroglobulin, or derivatives thereof. Derivatives include proteins which differ from BSA or thyroglobulin by amino acid substitution, addition, or deletion, or by post-translational modification.

In order to link the detection probe to the protein spacer it will generally be necessary to functionalise the detection probe. This can be done by the use of a modifier comprising a first reactive group capable of reacting with the detection probe and a second reactive group capable of reacting with the protein.

An example of a suitable modifier is 6-(Trifluoroacetylamino)hexyl-(2-cyanoethyl)-(N,N-diisopropyl)-phosphoramidite (C6-TFA). Other suitable modifiers will be known to those of ordinary skill in the art.

Once the modifier has reacted with the detection probe and the protein to link the detection probe to the protein the reacted modifier is termed herein a 'linker'.

The label or detection ligand may be part of or attached to a particle such as a bead. In such cases, preferably the protein is adsorbed directly to the label or the detection ligand.

The detection probe spacer may comprise a non protein. In a preferred arrangement, the detection probe spacer comprises a protein and a non protein, the detection probe being coupled to the non protein and the non protein being coupled to the protein thereby spacing the detection probe from the protein.

In order to link the non protein to the protein it will generally be necessary to use a modifier comprising a first reactive group capable of reacting with the non protein and a second reactive group capable of reacting with the protein. An example of a suitable modifier for use with non proteins which comprise a hydroxyl group is 6-(Trifluoroacetylamino)hexyl-(2-cyanoethyl)-(N,N-diisopropyl)-phosphoramidite (C6-TFA). Other suitable modifiers will be known to those of ordinary skill in the art.

Once the modifier has reacted with the non protein and the protein to link the non protein to the protein the reacted modifier is termed herein a 'linker'.

In other arrangements the detection probe spacer comprises a non protein only. With such arrangements it will generally be necessary to functionalise the non protein in order to link the non protein to the label or detection ligand. This can be done by the use of a modifier comprising a first reactive group capable of reacting with the non protein and a second reactive group capable of reacting with the label or detection ligand.

If the non protein comprises a hydroxyl group and the label or detection ligand comprises a carboxyl group, a suitable modifier comprises a phosphoramidite group and a primary amino group (or protected primary amino group which is deprotected before use). 6-(Trifluoroacetylamino)hexyl-(2-cyanoethyl)-(N,N-diisopropyl)-phosphoramidite (C6-TFA) is a suitable example. Other suitable modifiers will be known to those of ordinary skill in the art.

Examples of suitable non protein detection probe spacer components include 1',2'-Dideoxyribose phosphate (dS), 3-Hydroxypropyl phosphate ($S_{C3}$), and Hexaethyleneglycol phosphate (S).

Preferably, however, the non protein comprises a base capable of forming a stacking interaction with a base pair formed when the detection probe has hybridised to the target nucleic acid. More preferably the non protein comprises a nucleotide. Most preferably the non protein consists only of one or more nucleotides.

Preferably the non protein is at least the length of three nucleotides.

The detection probe spacer may be linked to any part of the detection probe which does not prevent the detection probe from hybridising to the target nucleic acid. If the detection probe spacer is linked to a part of the detection probe between the ends of the detection probe, one or both ends of the detection probe may be coupled to one or more nucleotides, preferably at least three nucleotides, which do not hybridise to the target nucleic acid when the detection probe has hybridised to the target nucleic acid.

Preferably the detection probe spacer is linked to one end of the detection probe. If the detection probe spacer is linked to one end of the detection probe, the end of the detection probe not linked to the detection probe spacer may be coupled to one or more nucleotides, preferably at least three nucleotides, which do not hybridise to the target nucleic acid when the detection probe has hybridised to the target nucleic acid.

The capture moiety may be capable of binding directly or indirectly to the target nucleic acid by base pairing or non base pairing interaction.

For example, the capture moiety may comprise a capture probe capable of hybridising directly to the target nucleic acid.

Alternatively, the capture moiety may comprise a capture probe capable of hybridising to a hook capture probe bound to the target nucleic acid.

The capture moiety may be capable of binding to a capture ligand coupled to a capture probe bound to the target nucleic acid, thereby allowing indirect binding of the capture moiety to the target nucleic acid. For example the capture moiety may be an antibody or antibody fragment. If the capture probe is coupled to a capture ligand, the capture probe may be linked to a capture probe spacer which is linked to the capture ligand to space the capture ligand from the capture probe.

The hook capture probe can be added to the sample solution so that it can bind to target nucleic acid in the sample solution and be captured by the capture probe as the sample solution wicks up the dipstick by capillary action.

The capture probe, the hook capture probe and the detection probe may each comprise at least one nucleic acid or nucleic acid analogue. Where a probe comprises more than one nucleic acid or nucleic acid analogue, they are preferably hybridised together.

The invention also provides a kit for testing for the presence of target nucleic acid in a sample solution which comprises:

a dipstick according to the second aspect of the invention in which the capture moiety is capable of binding to a is capture ligand coupled to a capture probe bound to the target nucleic acid; and a capture probe capable of hybridising to the target nucleic acid or to a hook capture probe bound to the target nucleic acid, wherein the capture probe is coupled to a capture ligand which can be bound by the capture moiety.

Examples of suitable labels include textile dyes, metal sol such as colloidal gold, and coloured particles such as coloured latex particles. Such labels can be coupled directly to the detection probe or, if the detection probe is coupled to a detection ligand, to the detection ligand binding moiety.

Examples of suitable capture or detection ligands include biotin (captured or detected for example by an anti-biotin antibody, avidin, streptavidin or a derivative thereof), fluorescein (captured or detected for example by an anti-fluorescein antibody) and 2,4-dinitrophenol (DNP) (captured or detected for example by an anti-DNP antibody).

The detection probe may comprise a universal detection probe which is capable of hybridising to a hook detection probe bound to the target nucleic acid. The universal detection probe may be linked to a label or a detection ligand thereby allowing detection of the detection probe.

It will be appreciated that kits and dipsticks of the invention may further comprise any reagent required for the kit to be used to detect target nucleic acid in a sample solution. For example, kits of the invention which comprise a detection probe coupled to a detection ligand may further comprise a detection ligand binding moiety. This may be separate to the dipstick or releasably immobilised to the dipstick between the contact end and the capture zone.

The detection ligand binding moiety may comprise an antibody or antibody fragment, or a non antibody. For example, if the detection ligand comprises biotin the detection ligand binding moiety may comprise an anti-biotin antibody, streptavidin, avidin or a derivative thereof which retains biotin binding activity. Preferably the detection ligand binding moiety is labelled thereby allowing indirect detection of target nucleic acid utilising the detection probe and the detection ligand binding moiety.

It will be understood that the invention relates to use of detection probes and/or capture probes linked to a spacer and that the detection probe or capture probe may be immobilised to the dipstick or incubated with the sample solution depending on the method of detection of target nucleic acid.

There is also provided according to the invention a kit for testing for the presence of target nucleic acid in a sample solution which comprises:

i) a dipstick comprising a chromatographic strip having a contact end for contacting the sample solution and a capture probe capable of hybridising to the target nucleic acid, or to a hook capture probe bound to the target nucleic acid, the capture probe being immobilised at a capture zone of the chromatographic strip remote from the contact end; and ii) a detection probe capable of hybridising to the target nucleic acid, the detection probe being coupled to a label allowing direct detection of the target nucleic acid utilising the detection probe, or the detection probe being coupled to a ligand allowing indirect detection of the target nucleic acid utilising the detection probe, wherein the label or the detection ligand is linked to a detection probe spacer and the detection probe spacer is linked to the detection probe thereby coupling the label or the detection ligand to the detection probe and spacing the label or the detection ligand from the detection probe.

There is also provided according to the invention a kit for testing for the presence of target nucleic acid in a sample solution which comprises:

i) a dipstick comprising a chromatographic strip having a contact end for contacting the sample solution and a capture moiety immobilised at a capture zone of the chromatographic strip remote from the contact end, the capture moiety being capable of binding directly or indirectly to the target nucleic acid;

ii) a capture probe capable of hybridising to the target nucleic acid, or to a hook capture probe bound to the target nucleic acid, wherein the capture probe is coupled to a capture ligand which can be bound by the capture moiety; and iii) a detection probe capable of hybridising to the target nucleic acid, the detection probe being coupled to a label allowing direct detection of the target nucleic acid utilising the detection probe, or the detection probe being coupled to a detection ligand allowing indirect detection of the target nucleic acid utilising the detection probe, wherein the label or the detection ligand is linked to a detection probe spacer and the detection probe spacer is linked to the detection probe thereby coupling the label or the detection ligand to the detection probe and spacing the is label or the detection ligand from the detection probe.

There is also provided according to the invention a kit for testing for the presence of target nucleic acid in a sample solution which comprises:

i) a dipstick comprising a chromatographic strip having a contact end for contacting the sample solution and a capture moiety immobilised at a capture zone of the chromatographic strip remote from the contact end;

ii) a capture probe capable of hybridising to the target nucleic acid, or to a hook capture probe bound to the target nucleic acid, wherein the capture probe is linked to a capture probe spacer and the capture probe spacer is linked to a capture ligand thereby coupling the capture ligand to the capture probe and spacing the capture ligand from the capture probe; and iii) a detection probe capable of hybridising to the target nucleic acid, the detection probe being coupled to a label allowing direct detection of the target nucleic acid utilising the detection probe, or the detection probe being coupled to a detection ligand allowing indirect detection of the target nucleic acid utilising the detection probe.

According to a further aspect of the invention there is provided a method for immobilising a probe to a solid phase which comprises providing a probe coupled to a protein and adsorbing the protein to the solid phase.

Methods of the invention for immobilising a probe to a solid phase may further comprise coupling the probe to the protein.

The probe is preferably coupled to a linker and the linker coupled to the protein. The probe is preferably coupled to the linker before the linker is coupled to the protein.

The probe may comprise a nucleic acid or nucleic acid analogue.

The linker is preferably coupled to a non nucleobase part of the probe. When the probe comprises nucleic acid, the linker is preferably coupled to a sugar or phosphate group of the probe. When the probe comprises a the nucleic acid analogue PNA (protein nucleic acid), the linker is preferably coupled to an amino group of the Probe. This is so that the linker does not interfere with base pairing of the nucleobase. Alternatively, the linker may be coupled to the 5' or 3' end of the part of the probe which is capable of hybridising to the binding partner of the probe (for example target nucleic acid) to avoid interference of the linker with the base pairing interactions of the probe and its binding partner.

The probe is preferably coupled to the linker by reaction of a phosphoramidite group attached to the linker with a hydroxyl group of the probe or by reaction of a hydroxyl group of the linker with a phosphoramidite group attached to the probe.

The linker is preferably coupled to the protein by reaction of a primary amino group attached to the linker with a carboxyl group of the protein.

The solid phase may comprise a membrane, preferably a nitrocellulose membrane. Alternatively, the solid phase may comprise a particle such as a bead.

There is also provided according to the invention a probe immobilised to a solid phase by adsorption to the solid phase of a protein coupled to the probe.

There is also provided according to the invention use of a dipstick, kit, or probe of the invention in a dipstick assay to test for the presence of target nucleic acid in a sample solution.

It is thought that the sensitivity of dipsticks of the invention having a capture probe spacer is improved because the capture probe linked to the capture probe spacer is more accessible for hybridisation to the target nucleic acid. The sensitivity of dipsticks or kits of the invention in which the capture probe is coupled to a capture ligand by a capture probe spacer may be improved because the capture probe is thereby more accessible for hybridisation to the target nucleic acid and the capture ligand is more accessible for binding by the capture moiety.

Similarly, it is thought that the sensitivity of dipsticks or kits of the invention having a detection probe spacer coupling the detection probe to a label is improved because the detection probe spacer makes the detection probe more accessible for hybridisation to the target nucleic acid. If the detection probe is coupled to a detection ligand by a detection probe spacer, the detection probe is thought to be more accessible for hybridisation to the target nucleic acid and the detection probe ligand may also be more accessible to the detection ligand binding moiety.

Use of spacers comprising nucleobases in accordance with the invention is thought to be particularly effective because the nucleotide or nucleobase is able to form stacking interactions with the base pairs formed between the capture is probe or the detection probe and the target nucleic acid. Formation of the stacking interactions is thought to enhance the hybridisation of the capture probe or the detection probe to the target nucleic acid thereby improving the efficiency of capture or detection of the target nucleic acid at the capture zone of the dipstick.

Where appropriate, dipsticks and kits of the invention may be used in the following types of dipstick assay to test for the presence of a target nucleic acid in a sample solution:

1) A dipstick is provided which comprises a chromatographic strip having a contact end and a capture probe immobilised at a capture zone remote from the contact end, the capture probe being capable of hybridising to the target nucleic acid. A detection probe is contacted with the sample solution under conditions for hybridisation of the detection probe to the target nucleic acid. The sample solution is contacted with the contact end of the dipstick to cause sample solution to move by capillary action to the capture zone, thereby allowing target nucleic acid and the detection probe to move with the sample solution to the capture zone, and target nucleic acid to be captured at the capture zone. Detection probe can then be detected for at the capture zone. The presence of detection probe at the capture zone indicates that target nucleic acid was present in the sample solution.

In a variation of this assay, the detection probe may be releasably immobilised to the dipstick between the contact end and the capture zone instead of being separate from the dipstick. When the contact end of the dipstick is contacted with the sample solution causing the sample solution to move by capillary action to the capture zone, the detection probe is released into the sample solution so that released detection probe can hybridise to target nucleic acid in the sample solution as it moves to the capture zone.

In further variations of this assay, the detection probe may be separate from the sample solution and contacted with the capture zone of the dipstick. This will usually be done after the contact end of the dipstick has been contacted with the sample solution. The detection probe may be contacted directly with the capture zone, or the detection probe may be in a separate probe solution which is contacted with the contact end of the dipstick to cause the probe solution to move by capillary action to the capture zone.

2) A dipstick is provided which comprises a chromotographic strip having a contact end and a capture moiety immobilised at a capture zone remote from the contact end, the capture moiety being capable of binding a capture probe hybridised to the target nucleic acid. The capture probe is contacted with the sample solution under conditions for hybridisation of the capture probe to the target nucleic acid. The sample solution is contacted with the contact end of the dipstick to cause sample solution to move by capillary action to the capture zone, thereby allowing target nucleic acid and the capture probe to move with the sample solution to the capture zone, and target nucleic acid to be captured at the capture zone by binding of the capture moiety to the capture probe. Target nucleic acid can then be detected for at the capture zone. Target nucleic acid may be detected using a detection probe as described for assay (1). The detection probe may be added to the sample solution with the capture probe or separately from the capture probe (in any order). Alternatively the detection probe may be releasably immobilised to the dipstick between the contact end and the capture zone, or may be contacted separately with the capture zone as described for assay (1).

In a variation of assay (2), the capture probe instead of being mixed with the sample solution, may be releasably immobilised to the dipstick between the contact end and the capture zone. When the contact end of the dipstick is contacted with the sample solution causing the sample solution to move by capillary action to the capture zone, the capture probe is released into the sample solution so that released capture probe is released into the sample solution so that released capture probe can hybridise to target nucleic acid in the sample solution as it moves to the capture zone. Target nucleic acid may be detected for using a detection probe which may be contacted with the sample solution, releasably immobilised to the dipstick between the contact end and the capture zone, or contacted separately with the capture zone.

In a further variation of assay (2), the capture probe may be contacted with the capture zone before, (or exceptionally, at the same time as) the sample solution reaches the capture zone by capillary action. This will allow the capture probe to be bound by the capture moiety at the capture zone so that target nucleic acid may be captured. The capture probe may be in a separate capture probe solution which is contacted separately with the capture zone by directly applying it to the capture zone, or by contacting the capture probe solution with the contact end of the dipstick to cause the capture probe to move by capillary action to the capture zone. Subsequent contact of is the contact end of the dipstick with the sample solution will allow target nucleic acid reaching the capture zone by capillary action to be captured there. Again, target nucleic acid may be detected for using a detection probe which may be contacted with the sample solution, releasably immobilised to the dipstick between the contact end and the capture zone, or contacted separately with the capture zone. As an alternative to use of a detection probe in assay (2), the target nucleic acid may be labelled directly in the sample solution, for example by covalent attachment of a label to the target nucleic acid. This may be achieved by contact of a precursor label with the sample solution and incubation of the sample solution and precursor label under conditions for covalent attachment of the label to target nucleic acid.

The capture moiety of assay (2) may be a universal capture probe capable of hybridising to the capture probe, or the capture moiety may be capable of binding by non base pairing interaction to the capture probe. For example, when the capture probe comprises one or more capture ligands, the capture moiety is a capture ligand binding moiety.

Where the dipstick assay uses more than one probe capable of hybridising to the target nucleic acid it is preferred that all the probes are added to the sample solution and that hybridisation is carried out in a single step. This simplifies the assay, making it easier and quicker to perform. It has been found that the sensitivity of detection of target nucleic acid using a one step hybridisation assay is about equal to the sensitivity of detection when hybridisation is carried out in multiple steps. Multiple step hybridisation may be carried out by sequential hybridisation of the different probes to the target nucleic acid in the sample solution, or by contacting the dipstick with different solutions each containing a different probe. Usually, the latter method of multiple step hybridisation will involve washing the dipstick between each contact with a different probe solution. Whilst there may be circumstances in which multiple step hybridisation is preferred, it will be appreciated that the simpler and quicker format of one step hybridisation will usually be preferred.

It is most preferred that the sample solution is of suitable composition to allow the hybridisation reactions to take place in a single hybridisation step and also to allow non base pairing interactions to take place (for example between a detection ligand and a detection ligand binding moiety and between a capture ligand and a capture ligand binding moiety) and transport a complex comprising target nucleic acid and one or more hybridised probes and (optionally) ligand binding moieties by capillary action up the dipstick. Using such a sample solution, it will be appreciated that the hybridisation reactions can then be carried out in a single step, and any ligand-ligand binding moiety interactions can take place, before the sample solution is contacted directly with the contact end of the dipstick (without the need to first dilute or alter the sample solution). Ligand-ligand binding moiety interactions can additionally or alternatively take place on the dipstick if desired as the sample solution travels to the capture zone. Simple and rapid dipstick detection of target nucleic acid is thereby facilitated.

We have found that such results are achieved with sample solutions comprising a standard hybridisation buffer (such as SSPE buffer or Tris buffer) with salt, detergent and a blocking protein such as BSA or powdered milk. The sensitivity of detection of target nucleic acid using such assays has been found to be about equal to or better than that of other dipstick assays.

Embodiments of the invention are now described by way of example with reference to the accompanying drawings in which.

Figure 3:
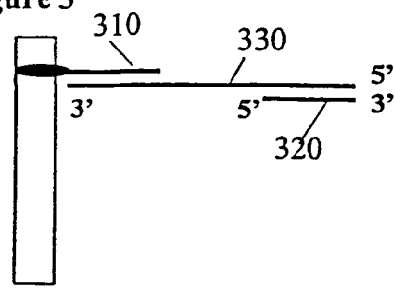
Figure 4:
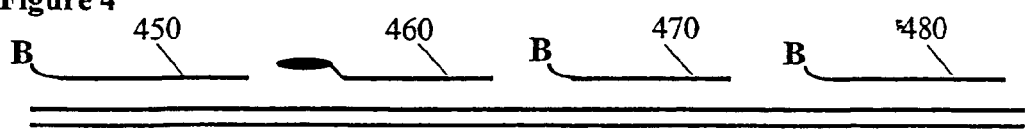
Figure 5:
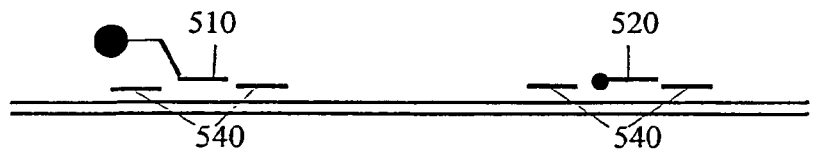
Figure 6:
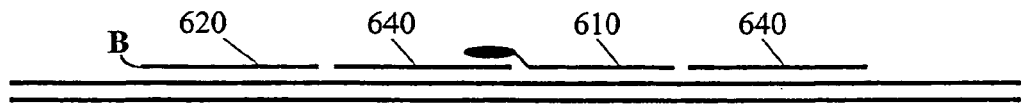
Figure 7:
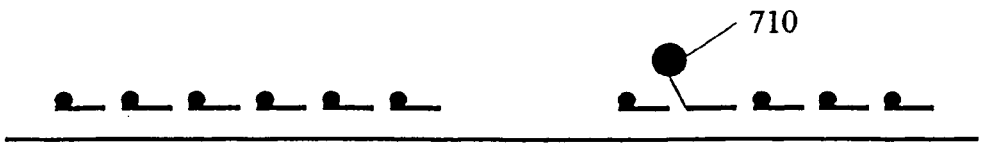
Figure 8:
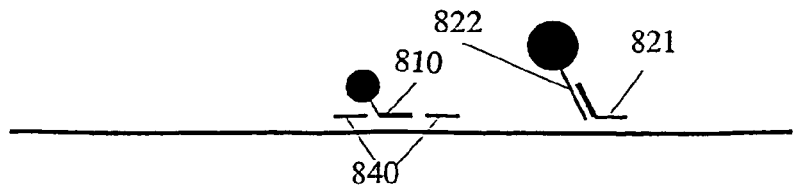
Figure 9:
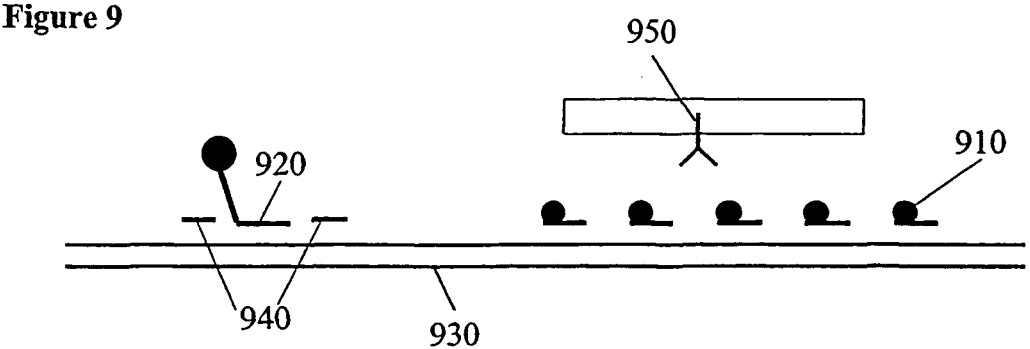
Figure 10:
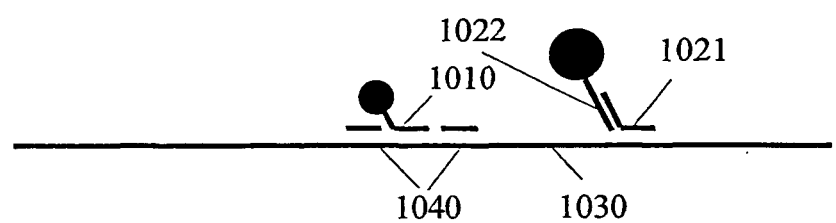
Figure 11:
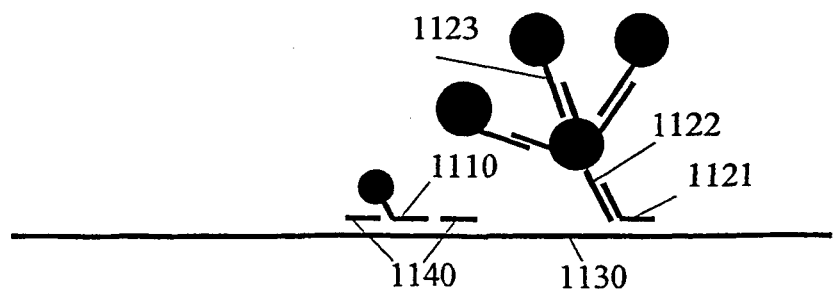
Figure 12:
Figure 12:
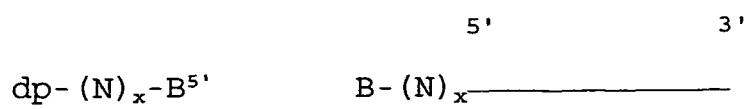
Figure 12:
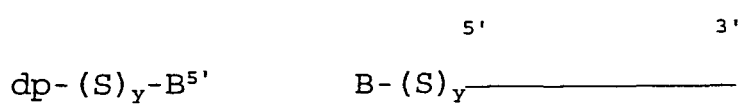
Figure 12:
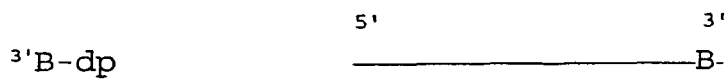
Figure 12:
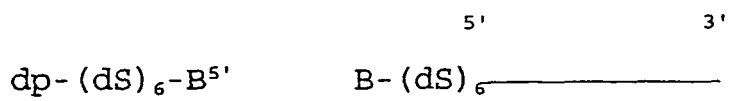
Figure 12:
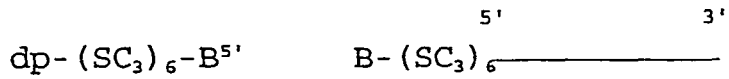
Figure 12:
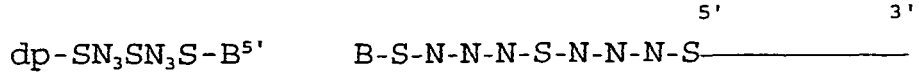

FIG. 3 shows the experimental setup for Example 1;
FIG. 4 shows the experimental setup for Example 2;
FIG. 5 shows the experimental setup for Example 3;
FIG. 6 shows the experimental setup for Example 4;
FIG. 7 shows the experimental setup for Example 6;
FIG. 8 shows the experimental setup for Example 7;
FIG. 9 shows the experimental setup for Example 9;
FIG. 10 shows the experimental setup for Example 10;
FIG. 11 shows the experimental setup for Example 11; and
FIG. 12 shows schematically the structures of different detection probes coupled to biotin detection ligand used in the examples.

The examples relate to detection of a DNA fragment of *Chlamydia trachomatis* (CT) cryptic plasmid DNA. CT is one of the most common causes of sexually transmitted disease. CT infections can cause infertility and, during pregnancy, can result in spontaneous abortion, still birth or postpartum endometritis. In neonates, CT infection can cause blindness and chronic respiratory disease. Approximately 10% of infected men and up to 70% of infected women do not show symptoms of CT infection. Consequently, accurate diagnosis of CT infection is important so that early treatment of the disease can be initiated.

Figure 2:
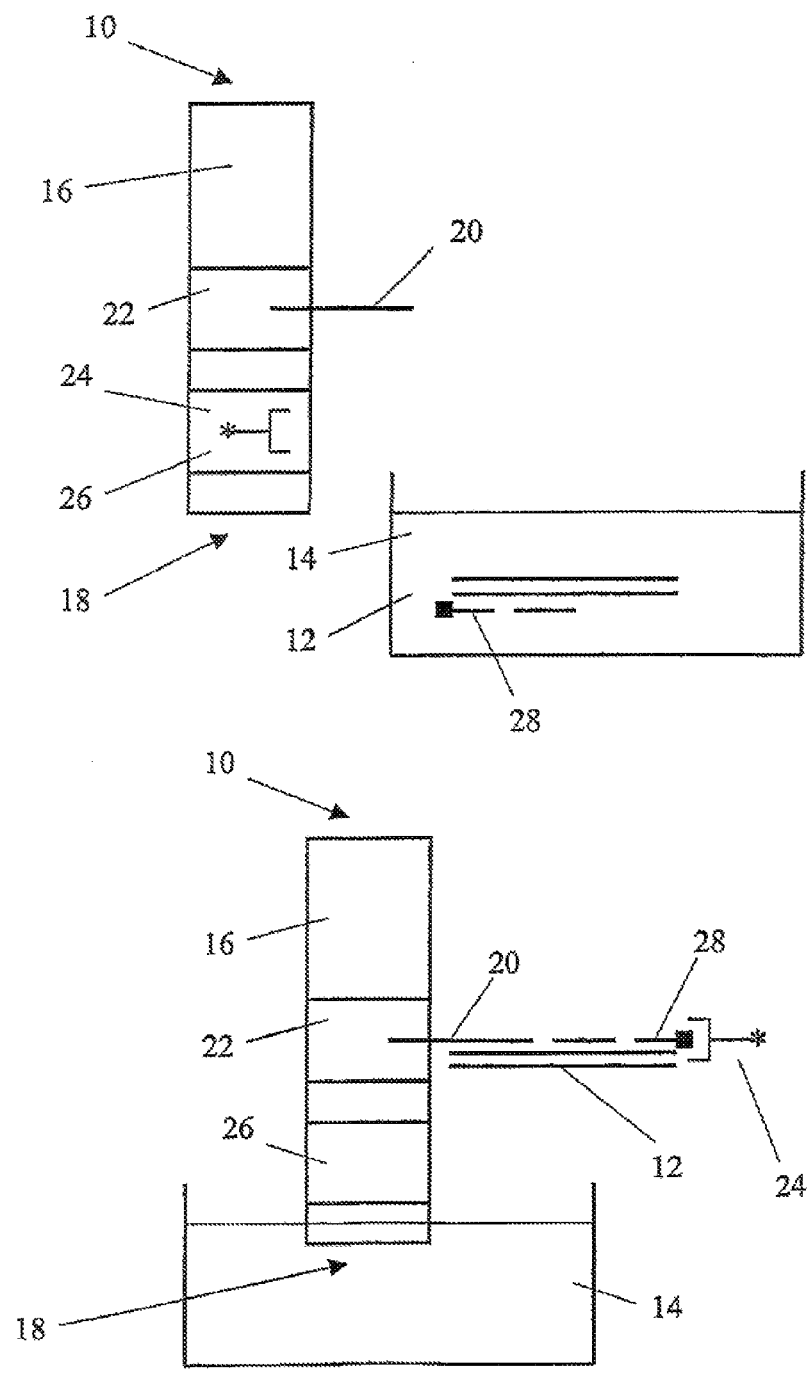
FIG. 2 shows detection of *Chlamydia trachomatis* target nucleic acid using an embodiment of the invention.

In the examples, a dipstick 10 is used to try to detect single or double stranded CT target nucleic acid 12 in a sample solution 14 (see FIG. 2). The dipstick 10 comprises a strip of nitrocellulose 16 having a contact end 18 for contacting the sample solution 14 and a capture probe 20 immobilised at a capture zone 22 of the nitrocellulose strip 16 remote from the contact end 18. An anti-biotin antibody-dye conjugate 24 (or an anti-fluorescein antibody-dye conjugate in example 5) is releasably immobilised at a conjugate zone 26 of the nitrocellulose strip located between the contact end 18 and the capture zone 22. The capture probe 20 is capable of hybridising to a first region of one strand (the first strand) of the target nucleic acid 12.

The sample solution 14 is prepared by spiking 1 ml urine with *Chlamydia trachomatis* bacteria then spinning the urine at 15K rpm for 30 minutes. The pellets are resuspended in 100 µl standard hybridisation buffer (including a blocking agent such as casein or BSA). A detection probe 28 capable of hybridising to the target nucleic acid is then added (together with a helper probe capable of hybridising to the target nucleic acid adjacent the region recognised by the detection probe and/or the capture probe if used). The detection probe 28 is coupled to biotin (or to fluorescein in example 5) (using methods well known to those of skill in the art). The sample solution 14 is then heated to 100° C. for 7 minutes and cooled.

The contact end 18 of the dipstick 10 is then contacted with the sample solution 14. The sample solution 14 and any target nucleic acid 12 hybridised to the detection probe 28 moves up the dipstick 10 by capillary action. As the sample solution 14 passes the conjugate zone 26, it mobilises the anti-biotin antibody-dye conjugate 24. Released anti-biotin antibody-dye conjugate 24 can then bind to the biotin coupled to the detection probe 28 hybridised to the target nucleic acid 12.

Complex formed between the anti-biotin antibody-dye conjugate 24, the detection probe 28 and the target nucleic acid 12 then moves up the dipstick 10 to the capture zone 22 where the target nucleic acid of the complex can hybridise to the immobilised capture probe 20. The capture probe 20 is immobilised at the capture zone 22 in such a way that it cannot be mobilised by the sample solution 14 as it moves past the capture zone 22. Consequently, the complex bound to the capture probe remains in the capture zone and can be detected by the presence of the dye of the anti-biotin antibody-dye conjugate at the capture zone.

If there is no CT target nucleic acid in the sample solution, the detection probe 28 cannot be captured at the capture zone 22 and so no dye is visible at the capture zone. If there is CT target nucleic acid in the sample solution, but insufficient amounts of the target nucleic acid can be captured at the capture zone the presence of the target nucleic acid in the sample solution will not be detected.

It has been found that the sensitivity of detection of target nucleic acid can be reduced if the distance between the region of the target nucleic acid to which the capture probe hybridises and the region to which the detection probe hybridises is less than 26 nucleotides. Thus, it is preferred that the distance between these regions is at least 26 nucleotides and preferably at least 200 nucleotides.

The capture of target nucleic acid described above is referred to as direct probe capture in the examples below. The strength of the detection of the target nucleic acid in the examples is recorded on a scale of 0 to 5, with 5 representing the strongest detection, and 0 no detection.

The sequences of the probes used in the following examples are:

```
                                    SEQ ID No 1:
5' TGC AAC TCT TGG TGG TAG ACT TTG C

SEQ ID No 2:
5' GCG CAC AGA CGA TCT ATT TTT TGC A

SEQ ID No 3:
5' CGG GCG ATT TGC CTT AAC CCC ACC A

SEQ ID No 4:
5' CCA AGC TTA AGA CTT CAG AGG AGC G

SEQ ID No 5:
5' CAT GCG TTT CCA ATA GGA TTC TTG G

SEQ ID No 6:
5' CAC AGT CAG AAA TTG GAG TGC TGG C

SEQ ID No 7:
5' CTT GCT GCT CGA ACT TGT TTA GTA C

SEQ ID No 8:
5' AGA AGT CTT GGC AGA GGA AAC TTT T

SEQ ID No 9:
5' CTA GAA TTA GAT TAT GAT TTA AAA GGG

SEQ ID No 10:
5' TTC ATA TCC AAG GAC AAT AGA CCA A

SEQ ID No 11:
5' TGA TCT ACA AGT ATG TTT GTT GAG T

SEQ ID No 12:
5' TGC ATA ATA ACT TCG AAT AAG GAG AAG

SEQ ID No 13:
5' TCC CTC GTG ATA TAA CTT ATC CG

SEQ ID No 14:
5' CAG GTT GTT AAC AGG ATA GCA CGC

SEQ ID No 15:
5' CTC GTT CCG AAA TAG AAA ATC GCA

SEQ ID No 16:
5' GGT AAA GCT CTG ATA TTT GAA GAC

SEQ ID No 17:
5' CTG AGG CAG CTT GCT AAT TAT GAG T
```

The structures of the detection probes in the examples described below are shown schematically in FIG. 12.

EXAMPLE 1

Experimental Setup

Capture format: direct probe capture (cp) Seq ID No 14 immobilised on the dipstick;

Detection probe (dp): Seq ID No 13 or Seq ID No 15 with biotin coupled directly to the 5'-end, or by a 3 nucleotide ($N_3$), 6 nucleotide ($N_6$), S, or SS spacer, or SEQ ID No 13 with biotin coupled directly to the 3'-end. $10^{12}$ copies of each.

Detection format: anti-biotin antibody-dye conjugate;

Target DNA: 73 or 76 nucleotide single stranded DNA fragments at $5 \times 10^{11}$-$10^{10}$ copies.

Results

| Detection probe | Copies of target: | | | |
|---|---|---|---|---|
| | $5 \times 10^{11}$ | $10^{11}$ | $5 \times 10^{10}$ | $10^{10}$ |
| | Signal strength | | | |
| dp Seq ID No 13 | | | | |
| dp-B5' | 3.5 | 3.0 | 2.0 | 1.0 |
| dp-$N_3$-B5' | 4.5 | 3.5 | 3.0 | 1.5 |
| dp-$N_6$-B5' | 5.0 | 4.0 | 3.0 | 2.0 |
| dp-S-B5' | 4.0 | 3.0 | 2.0 | 1.0 |
| dp-SS-B5' | 4.5 | 3.5 | 2.5 | 1.0 |
| 3'B-ap | 5.0 | 3.5 | 3.0 | 2.0 |
| dp Seq ID No 15 | | | | |
| dp-B5' | 3.5 | 2.0 | 1.0 | |
| dp-$N_3$-B5' | 4.0 | 3.0 | 2.0 | |
| dp-$N_6$-B5' | 4.5 | 3.0 | 2.0 | |
| dp-S-B5' | 4.0 | 2.5 | 1.5 | |
| dp-SS-B5' | 4.0 | 2.5 | 1.5 | |

These results show:

The sensitivity of target nucleic acid detection using detection probes with biotin coupled to the 5'-end by a $N_6$, $N_3$, SS or S spacer was higher than the sensitivity using a detection probe with biotin coupled directly to the 5'-end.

The $N_3$ and $N_6$ spacers were better than the S and SS spacers.

It is preferred that the biotin (or other detection ligand) is coupled to one end of the detection probe. In the complex formed when the capture probe and the detection probe are hybridised to the target nucleic acid at the capture zone then the biotin (or other detection ligand) can be at the end of the detection probe proximal to the region of the target nucleic acid which hybridises to the capture probe (internally orientated) or, preferably, at the end of the detection probe distal to the region of the target nucleic acid which hybridises to the capture probe (externally orientated). If no spacer is used to couple the detection ligand to the detection probe, then the sensitivity of detection of target nucleic acid is generally higher if the detection ligand is externally orientated. Consequently, the detection probe is usually chosen so that the detection ligand is externally orientated.

However, in this example, the sensitivity of detection using a detection probe with externally orientated biotin coupled directly to the 3'-end of the detection probe was as good as the sensitivity using a detection probe with internally orientated biotin coupled to the 5'-end of the is detection probe by a six nucleotide spacer. Thus, when spacers are used in accordance with the invention, the detection probe does not have to be chosen so that the detection ligand is externally orientated in the complex captured at the capture zone.

EXAMPLE 2

Experimental Setup

Capture format: direct probe capture (cp) Seq ID No 14 immobilised on dipstick membrane;

Detection probe: detection probe (dp) Seq ID No 13, Seq ID No 15 and Seq ID No 16 with biotin coupled to the 5'-end by a 3 nucleotide ($N_3$), 6 nucleotide ($N_6$), S or SS spacer. $10^{12}$ copies of each.

Detection format: anti-biotin antibody-dye conjugate;

Target DNA: 214 bp double stranded DNA fragments at $10^{11}$-$10^{10}$ copies.

Results

| Detection probe | Copies of target: | | |
|---|---|---|---|
| | $10^{11}$ | $5 \times 10^{10}$ | $10^{10}$ |
| | | Signal Strength | |
| dp13-B + dp15-B + dp16-B | 1.5 | 1.0 | 0.0 |
| dp13-$N_3$-B + dp15-$N_3$-B + dp16-$N_3$-B | 3.0 | 2.0 | 0.5 |
| dp13-$N_6$-B + dp15-$N_6$-B + dp16-$N_6$-B | 4.5 | 3.0 | 1.0 |
| dp13-S-B + dp15-S-B + dp16-S-B | 3.0 | 2.0 | <0.5 |
| dp13-SS-B + dp15-SS-B + dp16-SS-B | 3.5 | 3.0 | 0.5 |
| dp13 non-lab + dp15-$N_6$-B + dp16-$N_6$-B | 2.5 | 1.5 | 0.5 |

These results show:

The sensitivity of detection of double stranded target nucleic acid was improved more than five-fold using $N_3$, $N_6$, S or SS spacers.

The sensitivity of detection was higher with the $N_6$ and SS spacers than with the $N_3$ and S spacers, indicating that the length of the spacer is important for improved sensitivity of detection.

The sensitivity of detection was higher with the $N_6$ spacer than the SS spacer, despite the fact that these spacers are of equivalent length, indicating that the physicochemical properties of the spacer are important for improved sensitivity of detection.

The sensitivity of detection using only two detection probes each coupled at the 5'-end to biotin by an $N_6$ spacer (dp13 non-lab+dp15-$N_6$-B+dp16-$N_6$-B), in which the biotin is internally orientated in the complex captured by the capture probe, was greater than the sensitivity of detection using three detection probes each coupled at the 5'-end directly to biotin (dp13-B+dp15-B+dp16-B) in which the biotin of one detection probe (dp13-B) is externally orientated in the complex captured by the capture probe.

Conclusions from Examples 1 and 2

The sensitivity of target nucleic acid detection is increased by using a spacer to couple the detection ligand to the detection probe.

Longer spacers are better than shorter spacers.

Spacers of equivalent length but with different physicochemical properties had different effects on the sensitivity of detection. In particular, spacers in which the non protein component consists only of nucleotides are better than spacers which include non nucleotide components. Possible explanations for this are:

1. Nucleotide spacers may improve the sensitivity of detection by enhancing hybridisation of the detection probe to the target nucleic acid. The nucleotides of these spacers are not expected to base pair to nucleotides of the target nucleic acid when the detection probe hybridises to the target nucleic acid. The nucleobases of these nucleotides may form stacking interactions with the base pairs formed when the detection probe hybridises to the target nucleic acid. These stacking interactions may enhance the stability of the hybrid formed between the target nucleic acid and the detection probe, thereby enhancing the sensitivity of detection of target nucleic acid.

2. Nucleotide spacers may be more rigid than the S and SS spacers. The ribose rings of the nucleotide spacers are expected to provide much more rigidity than the polyethylene glycol groups of the S and SS spacers. This greater rigidity might increase the availability of the detection ligand coupled to the nucleotide spacer for interaction with the detection ligand binding moiety.

3. Polarity differences between the nucleotide and non nucleotide spacers may cause differences in the sensitivity of detection.

EXAMPLE 3

Experimental Setup

Capture format: direct probe capture (cp) Seq ID No 10 immobilised on the dipstick;

Detection probe: detection probe (dp) Seq ID No 13 coupled to biotin at the 5'-end either directly or by a $N_6$, SS, $(dS)_6$, $(SC_3)_6$ or $SN_3SN_3S$ spacer. $10^{12}$ copies of each.

Detection format: anti-biotin antibody-dye conjugate;

Helper probes: SEQ ID No 5 and SEQ ID No 6 adjacent to SEQ ID No 10; SEQ ID No 1 and SEQ ID No 2 adjacent to SEQ ID No 13 at $10^{12}$ copies;

Target DNA: 872 bp double stranded DNA fragment at $2 \times 10^{11}$-$5 \times 10^{10}$ copies.

Results

| Detection Probe | Copies of target: | |
|---|---|---|
| | $2 \times 10^{11}$ | $5 \times 10^{10}$ |
| | Signal strength | |
| dp-B | <1.0 | 0.0 |
| dp $N_6$-B | 2.0 | 0.5 |
| dp-SS-B | 1.0 | 0.0 |
| dp-$(dS)_6$-B | 1.0 | 0.0 |
| dp-$(SC_3)_6$-B | 1.0 | 0.0 |
| dp-$SN_3SN_3S$-B | 1.5 | 0.0 |

These results show:

The SS, $(dS)_6$, and $(SC_3)_6$ spacers are of equivalent length and had a similar effect on enhancing the sensitivity of detection of target nucleic acid despite their structural differences and properties.

The $N_6$ spacer is of equivalent length to the SS, $(dS)_6$, and $(SC_3)_6$ spacers. However, the $N_6$ spacer had the greatest effect on improving the sensitivity of detection of target nucleic acid.

The sensitivity of target nucleic acid detection was greater using the $N_6$ spacer than the $SN_3SN_3S$ spacer (the longest spacer tested). A possible explanation for this could be that the S monomer reduces or eliminates stacking interaction between the nucleobases of the $N_3$ components of the spacer and the base pairs formed between the detection probe and the target nucleic acid. This data supports the conclusion that stacking interactions between unpaired nucleobases of the spacer and the duplex formed between the target nucleic acid and the detection probe are important in enhancing the sensitivity of detection of target nucleic acid.

EXAMPLE 4

Spacers with different physicochemical properties and lengths were evaluated by the dipstick test and by dot blot analysis. Dot blot analysis enables the efficiency of the interaction of the anti-biotin antibody with the biotin coupled to the detection probe to be analysed in the absence of hybridisation of the detection probe to the target nucleic acid. $5 \times 10^8$-$5 \times 10^{11}$ copies of detection probes coupled to biotin by different spacers were spotted at different places on a positively charged nylon membrane and UV cross-linked to the membrane. The membrane was then incubated with an anti-biotin antibody coupled to alkaline phosphatase (capable of converting a Nitro Blue Tetrazolium/5-Bromo-4-Chloro-3-Indolyl Phosphate (NBT/BCIP) chromogenic substrate), washed, and incubated with the NBT/BCIP chromogenic substrate, and the membrane was observed to see if any colour formed at the capture zone.

Experimental Setup for Dipstick Test

Capture format: direct probe capture (cp) Seq ID No 14 immobilised on the dipstick;

Detection probe: detection probe (dp) Seq ID No 13 coupled to biotin at the 5'-end either directly or by a nucleotide or non-nucleotide spacer. $10^{12}$ copies of each.

Detection format: anti-biotin antibody-dye conjugate;

Helper probes: SEQ ID No 2 and SEQ ID No 3 adjacent to SEQ ID No 14 at $10^{12}$ copies;

Target DNA: 416 bp double stranded DNA fragment at $5 \times 10^{10}$-$5 \times 10^9$ copies.

Results

|                 | copies of target;      |                    |
|-----------------|------------------------|--------------------|
| Detection probe | $5 \times 10^{10}$ Signal strength | $5 \times 10^9$ |
| dp-B$^{5'}$     | 3.5                    | 0.5                |
| dp-N$_3$-B$^{5'}$ | 4.5                  | 1.5                |
| dp-N$_4$-B$^{5'}$ | 4.5                  | 1.0                |
| dp-N$_5$-B$^{5'}$ | 4.5                  | 1.0                |
| dp-N$_6$-B$^{5'}$ | 5.0                  | 1.5                |
| dp-(dS)$_6$-B$^{5'}$ | 4.0               | 0.5                |
| dp-S-B$^{5'}$   | 3.5                    | 0.0                |
| dp-SS-B$^{5'}$  | 4.0                    | 0.0                |
| dp-SSS-B$^{5'}$ | 4.5                    | 0.0                |
| dp-SSSS-B$^{5'}$ | 4.0                   | 0.0                |
| dp-S N$_3$ S N$_3$ S-B$^{5'}$ | 4.5      | 0.5                |

Experimental Setup for Dot-Blot Analysis

Detection probes: detection probe Seq ID No 13 coupled to biotin at the 5'-end, either directly or by a nucleotide or non-nucleotide spacer.

Detection format: anti-biotin antibody coupled to alkaline phosphatase, detection by NBT/BSIP chromogenic substrate.

Results

| Spacer       | Detection limit     |
|--------------|---------------------|
| without      | $5.0 \times E11$    |
| N$_3$        | $5.0 \times E10$    |
| N$_4$        | $5.0 \times E10$    |
| N$_5$        | $5.0 \times E10$    |
| N$_6$        | $2.5 \times E10$    |
| (dS)$_6$     | $2.5 \times E10$    |
| SN$_3$SN$_3$S | $2.5 \times E9$    |
| SSSS         | $2.5 \times E9$     |
| SSS          | $5.0 \times E9$     |
| SS           | $2.5 \times E10$    |
| S            | $5.0 \times E11$    |

The results of the dipstick test show:

There is no significant difference in the sensitivity of target nucleic acid detection using detection probes with three, four or five nucleotide spacers.

The sensitivity of detection with a six nucleotide spacer is marginally better than 3-5 nucleotide spacers.

The sensitivity of detection with spacers consisting only of nucleotides was better than with spacers which include non-nucleotides. For example the N$_3$ spacer was better than the longest spacer SN$_3$SN$_3$S, equivalent to 15 nucleotides in length.

The (dS)$_6$ spacer is slightly better than the SS spacer.

The results of the dot-blot test show:

The sensitivity of detection was highest with the longest spacers (SSSS and SN$_3$SN$_3$S).

The sensitivity of detection using equivalent length spacers (N$_6$, (dS)$_6$ and SS) with different physicochemical properties was similar.

Conclusions from Examples 3 and 4

The dS component has a similar structure to a nucleotide. Both have a ribose residue, expected to provide rigidity. However, the nucleotide has a nucleobase which is not present in the dS component. The different effect of the (dS)$_6$ spacer on the sensitivity of target nucleic acid detection compared to the N$_6$ spacer suggests that the greater effect on the improvement of sensitivity of detection using a nucleotide spacer is explained principally by the presence of the nucleobases which do not base pair with the target nucleic acid.

The composition of the spacer appears to be more important than its length (compare the results for dp-N$_3$-B$^{5'}$ and dp-SN$_3$SN$_3$S-B$^{5'}$ in the dipstick test of example 4).

The sensitivity of detection using a (dS)$_6$ spacer was greater than with an SS spacer. These spacers are of equivalent length. This suggests that the physicochemical properties of the spacer, such as rigidity or polarity, may also have an effect on the improvement of sensitivity of detection by the spacer.

The dot blot analysis of example 4 shows that the length of the spacer is important for the availability of the biotin to the anti-biotin antibody. The sensitivity of biotin recognition by the anti-biotin antibody was similar whether the biotin was coupled to the immobilised probe by an N$_6$, (dS)$_6$ or SS spacer. However, the effect of these spacers on the sensitivity of detection in the dipstick test of example 4 was different. This suggests that the composition of the spacer is more important in the hybridisation of the detection probe to the target nucleic acid than in the recognition of the biotin by the anti-biotin antibody. The length of the spacer appears to be more important than the composition of the spacer for recognition of the biotin (or other detection ligand) by the anti-biotin antibody (or other detection ligand binding moiety).

EXAMPLE 5

Experimental Setup

Capture format: direct probe capture (cp) Seq ID No 14 coupled to BSA immobilised to the dipstick. The capture probe is coupled to the BSA either directly or by a six nucleotide spacer;

Detection probe: detection probe (dp) Seq ID No 13 coupled to fluorescein. $10^{12}$ copies.

Detection format: anti-fluorescein antibody-dye conjugate;

Target DNA: 73 nt or 76 nt single stranded DNA fragments at $10^{11}$ copies.

Result:

| capture probe       | Copies of target: $10^{11}$ signal strength |
|---------------------|---------------------------------------------|
| cp-BSA-dipstick     | 4.0                                         |
| cp-N$_6$-BSA-dipstick | 5.0                                       |

EXAMPLE 6

Experimental Setup

Capture format: direct probe capture (cp) Seq ID No 14 coupled at the 5'-end to BSA immobilised on the dipstick. The capture probe is coupled to the BSA by an N$_6$ or SN$_3$SN$_3$S spacer;

Detection probes: detection probes (dp) Seq ID No 7, 8, 9, 10, 11, 12, 13, 15, 16 and 17 coupled to biotin. $10^{12}$ copies of each;

Detection format: anti-biotin antibody-dye conjugate;

Target: 872 bp double stranded DNA at $10^{11}$-$2.5 \times 10^9$ copies.

Result

|  | Copies of target: | | | | |
|---|---|---|---|---|---|
| Capture probe | $10^{11}$ | $2.5 \times 10^{10}$ | $10^{10}$ | $5 \times 10^9$ | $2.5 \times 10^9$ |
|  | signal strength | | | | |
| cp-SN$_3$SN$_3$S-BSA-dipstick | 4.0 | 3.5 | 2.5 | 1.0 | 0.0 |
| cp-N$_6$-BSA-dipstick | 4.5 | 4.0 | 3.0 | 1.5 | 0.0 |

EXAMPLE 7

Experimental Setup

Capture format: direct probe capture (cp) Seq ID No 15 coupled to BSA immobilised on the dipstick. The capture probe is coupled to the BSA by an N$_6$ spacer;

Helper probes: SEQ ID No 3 and SEQ ID No 4 adjacent to SEQ ID No 15;

Detection probe: In this example, the detection probe comprises a hook probe and a universal probe. The hook probe has sequence corresponding to Seq ID No 17 (capable of hybridising to the target nucleic acid) and sequence complementary to the sequence of a universal probe. The universal probe is coupled to a textile dye by an N$_6$ or SN$_3$SN$_6$ spacer. There are $10^{12}$ copies of the hook probe.

Target: 872 bp double stranded DNA at $10^{11}$ and $10^{10}$ copies.

Result

|  | Copies of target: | |
|---|---|---|
|  | $10^{11}$ | $10^{10}$ |
| Capture probe | signal strength | |
| Universal probe-SN$_3$SN$_6$-Dye | 2.0 | 0.0 |
| Universal probe-N$_6$-Dye | 2.0 | 0.5 |

Conclusions from Examples 5, 6, and 7

Use of spacers comprising a protein immobilised to the dipstick and a non protein to couple the capture probe to the immobilised protein (examples 5 and 6), or use of non protein spacers to couple the label to the detection probe (example 7) improve the sensitivity of detection of target nucleic acid.

The sensitivity of nucleic acid detection was highest when the non protein component of the spacer consisted entirely of nucleotides.

EXAMPLE 8

The sensitivity of target nucleic acid detection using a capture probe immobilised on the dipstick membrane by a protein carrier or by passive adsorption are compared in this example.

10 nmoles of capture probe functionalised at the 5'- or 3'-end with a primary amino group was mixed with 1 µl 10% BSA and 25 µl of 50 mM MES buffer (pH 6.1) and made up to 49 µl with water in a 500 µl microfuge tube. 1 µl of coupling reagent (freshly prepared 300 mM 1-Ethyl-3-(3-dimethylaminopropyl)carbodiimide (EDAC) in water) was then added and mixed in well. The mixture was left at room temperature overnight to couple the BSA to the capture probe, and then stored at 2-8° C. The BSA-capture probe was then applied to the capture zone of the dipstick and the dipstick was heated at 80° C. for 1 hour.

The molar ratio of capture probe to BSA and the concentration of the EDAC coupling reagent was optimised. Capture probe:BSA ratios of 2.7:1, 3.2:1, 4.1:1, 5.2:1, 6.6:1, 10.9:1 were studied. 1, 1.5, 2, 4, 5 and 20 mM concentrations of EDAC were studied. Concentrations higher than 5 mM caused the BSA-capture probe to precipitate out of the solution.

Experimental Setup

Capture format: direct probe capture by Seq ID No 14 immobilised directly on the dipstick membrane or by a BSA protein spacer. The capture probe and the capture probe-BSA were applied to the dipstick and immobilised by treating the dipstick for 1 h at 80° C.

Detection probe: biotin labelled detection probe (dp) Seq ID No 13 at $10^{12}$ copies.

Detection format: anti-biotin antibody-dye conjugate;

Target DNA: 73 nucleotide single stranded DNA fragments at $1 \times 10^{11}$ copies.

Results

| Capture probe: | Signal |
|---|---|
| capture probe-BSA | 4.0 |
| Capture probe | 0.0 |

Conclusion

The target nucleic acid was undetected using a capture probe directly immobilised to the dipstick. However, a strong detection signal was obtained if the capture probe was coupled to BSA and the BSA was immobilised to the dipstick.

The following examples relate to detection of target nucleic acid using a probe coupled to a coloured particle by a protein spacer. Coloured dye particles were coated with probe coupled to BSA. The protein is adsorbed to the dye particles thereby coupling the probe to the dye particles. The procedure used was as follows:

Dilute 11 µl of washed dye ($A_{575}$=900) in 434 µl of 10 mM phosphate buffer containing 10 mM NaCl, 1 mM EDTA, pH 7.5. Add 5 µl of probe-BSA (2 mg/ml), mix well and rotate at room temperature for 1 hour;

Add 50 µl of 20% alkaline treated casein. Mix well and rotate at room temperature for 1 hour;

Centrifuge at 4000 rpm in microfuge at room temperature for 15 min;

Remove supernatant and resuspend the pellet in 500 µl of conjugation buffer containing 5% sucrose 2% alkaline treated casein, 0.02% Na azide.

EXAMPLE 9

Experimental Setup

Capture format: Anti-biotin antibody/biotin coupled to capture probes Seq ID No 13, No 14, No 15, No 16 and No 17 at $10^{12}$ copies per test.

Alternatively direct probe capture format (Seq ID No 14 or Seq ID No 15) were used for comparison;

Direct detection probe Seq ID No 10 coupled to dye particle by BSA;

Helper probes: SEQ ID No 5 and SEQ ID No 6 adjacent to SEQ ID No 10;
Target: 872 bp ds DNA at $10^{11}$ to $10^8$ copies.
Result

| Signal Amplification Using Multiple Probes | | | | | | |
|---|---|---|---|---|---|---|
| Capture probe(s) | Seq ID No 13 | Seq ID No 14 | Seq ID No 15 | Seq ID No 16 | Seq ID No 17 | All 5 |
| Signal Strength $10^{11}$ copies target | 1 | 0 | 1 | 1 | 1 | 5 |

| Sensitivity Analysis | | | | | | |
|---|---|---|---|---|---|---|
| Target copies | $1 \times 10^{11}$ | $1 \times 10^{10}$ | $5 \times 10^9$ | $1 \times 10^9$ | $5 \times 10^8$ | $1 \times 10^8$ |
| Antibody Capture (5 probes) | 5 | 4.5 | 4 | 2.5 | 2 | 0.5 |
| Direct Probe Capture (Seq ID No 15) | 4.5 | 3 | 2.5 | 1.5 | 0 | 0 |
| Direct Probe Capture (Seq ID No 14) | 3 | 2 | 0.5 | 0 | 0 | 0 |

These results show that direct detection probe-dye conjugate works with both antibody capture format and direct probe capture format.

EXAMPLE 10

Experimental Setup
Capture format: direct probe capture (cp) Seq ID No 15 coupled to BSA immobilised to the dipstick.
Helper probes: SEQ ID No 3 and SEQ ID No 4 adjacent to SEQ ID No 15;
Detection probe region Seq ID No 17. A "hook probe" with sequence complimentary to target DNA in this region and to the universal probe sequence was used at $10^{12}$ copies per test;
Detection format: Textile dye coupled to the universal probe by BSA;
Target: 872 bp ds DNA at $10^{11}$ and $10^{10}$ copies.
Result:

| Copies of target | $10^{11}$ | $10^{10}$ |
|---|---|---|
| signal | 2.0 | 0.0 |

The advantage of this format in comparison with direct detector probe dye conjugate format is that it allows an application of universal reagent for visual detection of nucleic acid when a probe of universal nucleotide sequence is conjugated to coloured particles.

EXAMPLE 11

Experimental Setup
Capture format: direct probe capture Seq ID No 15 coupled to BSA immobilised to the dipstick.
Helper probes: SEQ ID No 3 and SEQ ID No 4 adjacent to SEQ ID No 15;
Detection probe region Seq ID No 17. A "hook" detection probe 1, with sequence complementary to target DNA in this region and to the universal probe sequence 2, was used at $10^{12}$ copies per test;

Detection format: a hook detection probe comprises sequence complementary to sequence of the target nucleic acid and to the sequence of a first universal detection probe. The first universal detection probe is coupled to BSA and the BSA is adsorbed to a first coloured particle thereby coupling the first universal detection probe to the first coloured particle. Several second universal detection probes are also each coupled to BSA adsorbed to the first coloured particle. The second universal detection probes comprise sequence complementary to sequence of a third universal detection-probe. The third universal detection probe is coupled to BSA adsorbed to a second coloured particle. When target nucleic acid is detected using the hook detection probe, the first, second and third universal detection probes and the first and second coloured particles, a single first coloured particle forms a first layer on the target nucleic acid and several second coloured particles form a second layer on the target nucleic acid as in FIG. 11. Because several coloured particles can be attached to each target nucleic acid in this way, it is thought that the sensitivity of detection of target nucleic acid is improved compared to use of a hook detection probe and a single universal detection probe coupled to a coloured particle.

Target: 872 bp ds DNA at $10^{11}$ and $10^{10}$ copies.
Results:

| Copies of target | $10^{11}$ | $10^{10}$ |
|---|---|---|
| signal | 2.0 | 0.5 |

Similar results were obtained with 1598 bp ds DNA target.

EXAMPLE 12

One-Step Nucleic Acid Dipstick Assay Detection of *Chlamydia trachomatis*
Experimental Set-Up:
Reagents:
Capture Format: oligonucleotide probe capture immobilised on dipstick membrane via BSA carrier;
Detection format: multiple biotin labelled detector probe; anti-biotin antibody-colloidal gold conjugate;
Sample preparation: *Chlamydia trachomatis* (Ct) elementary bodies (EB) celles were prepared in concentrations from $10^6$ copies/µl to $10^3$ copies/µl in PBS buffer and heated at 100° C. for 20 minutes;

Hybridisation/dipstick running buffer: Standard hybridisation buffer comprising salt, detergent and a blocking protein such as BSA or powdered milk.

Method:

The detection probe, helper probe and $5\times10^6$-$5\times10^3$ copies of EB diluted in hybridisation buffer made up to 80 µl and heated at 100° C. for 7 minutes. The mixture was then centrifuged briefly to collect all the liquid and mixed with 20 µl anti-biotin Ab colloidal gold. The whole 100 µl mixture were wicked up on dipstick and let to develop a signal.

Results and Discussion

Figure 13:
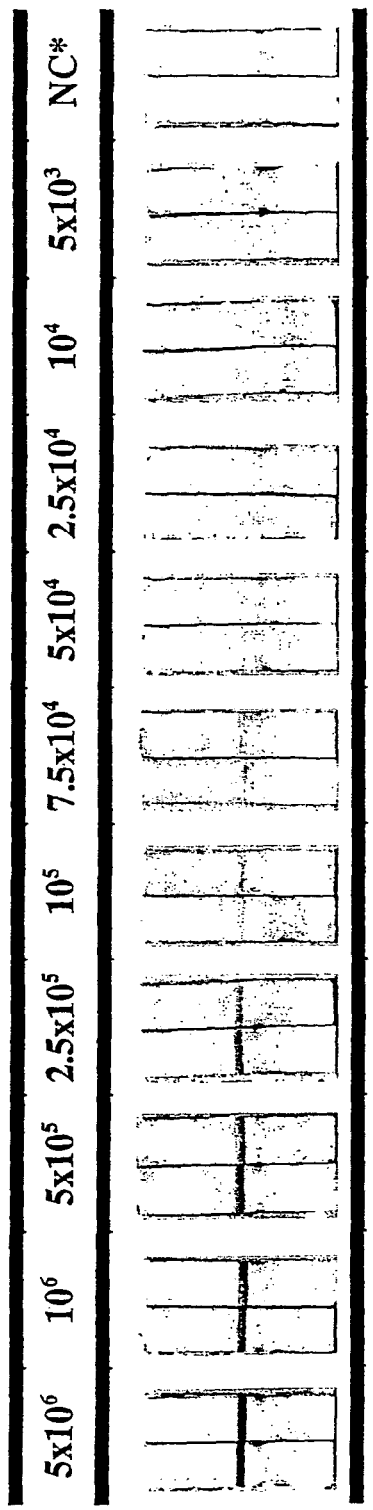

The results presented in the Table and FIG. 13 showed that about $10^4$ copies of Ct EB could be detected with one step nucleic acid dipstick assay in less than an hour including the sample preparation step.

Although the so presented dipstick detection assay has a sensitivity of detection about equal to other sandwich hybridisation assays it has the major advantages of speed and simplicity.

A sandwich hybridisation assay for detection of Ct disclosed in PCT WO 93/1322 for example, is a complex multi-component microtitre plate format assay, which could not be accomplished for less than 5 hours. This assay is a multi-step assay, which requires a gradual addition of its components in a defined order with incubations and washing steps after the addition of every new component.

The nucleic acid dipstick assay subject of this invention could be done in one step with no need of different steps for addition of components and washings. This sandwich hybridisation assay does not require more than one solution conditions in order to render them advantageous for hybridisation and other affinity pair formations. The same solution conditions could serve a free migration of the components through the dipstick membrane as well.

The sensitivity of detection of single and double stranded target nucleic acid by dipsticks has been found to be significantly improved by the use of spacers in accordance with the invention. The sensitivity of detection of double stranded circular target nucleic acid can also be increased by use of spacers in accordance with the invention.

Single stranded target nucleic acid is known to form secondary structure by means of intramolecular base pairing interactions. Such secondary structure can inhibit binding of the capture probe and the detection probe to the target nucleic acid. Consequently, the region of the target nucleic acid to which the detection probe and capture probe bind is often chosen as a region predicted to be substantially free of secondary structure.

The improved sensitivity of detection of double stranded target nucleic acid achieved by use of spacers in accordance with the invention means that the sensitivity of detection of single stranded target nucleic acid using a capture probe and/or a detection probe which recognises a region of the target nucleic acid involved in secondary structure will also be improved. An advantage of this is that the capture probe and/or detection probe may not have to be chosen based on predictions of the secondary structure formed by the target nucleic acid, thus simplifying the choice of capture and detection probe.

Conventional methods of dipstick detection are thought to be very poor at detecting circular double stranded target nucleic acid. Consequently, such target nucleic acid is usually treated with an enzyme that linearises the double stranded target before the target is detected. Improved detection of circular double stranded target nucleic acid using spacers in accordance with the invention means that linearisation of the target nucleic acid may not be required, thus simplifying the detection methods.

FIGURE LEGENDS

Figure 1:
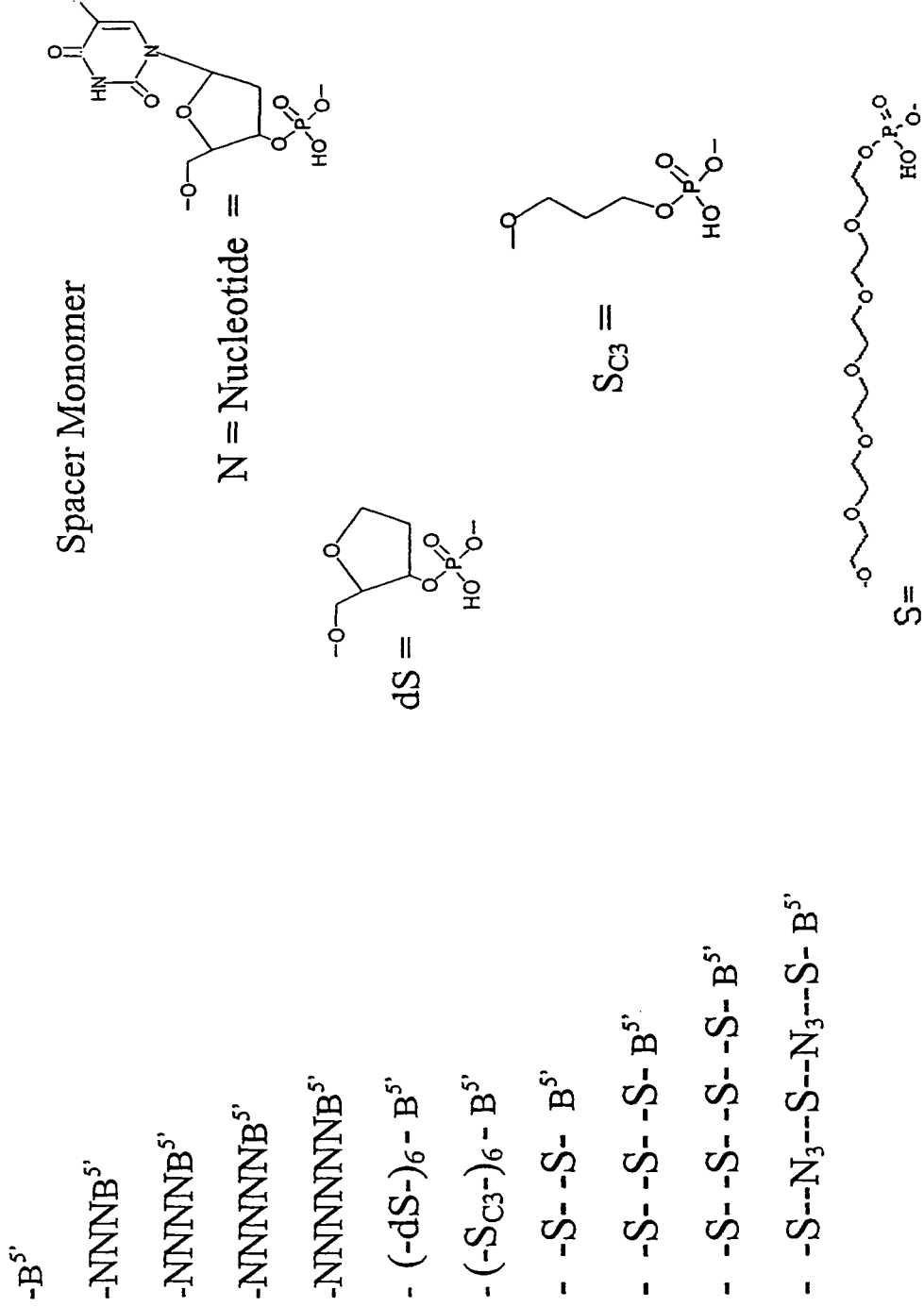
FIG. 1 shows the chemical structure of non protein components suitable as components of the capture probe spacer or the detection probe spacer of the invention.

FIG. 1—Design of Spacer
B=biotin coupled to a linker
FIG. 3
310—cp
320—dp
330—target
FIG. 4
450—dp Seq ID No 13
460—cp Seq ID No 14
470—dp Seq ID No 15
480—dp Seq ID No 16
FIG. 5
510—cp
520—dp
540—helper probes
FIG. 6
610—cp
620—dp
640—hp
FIG. 7
710—cp-$N_6$-BSA or cp-$SN_3$-$SN_3$-S-BSA
FIG. 8
810—cp
821—detection hook
822—Universal probe-$N_6$-Dye or Universal probe-$SN_3$-$SN_6$-Dye
840—helper probes
FIG. 9
910—capture probe coupled to biotin
920—detection probe coupled to dye particle by BSA
930—872 bp dsDNA Target
940—helper probes
950—membrane bound anti-biotin antibody
FIG. 10
1010—cp
1021—detection hook
1022—Universal probe-Dye
1040—helper probes
FIG. 11
1110—direct probe capture
1121—hook probe
1122—first layer dye conjugate
1122—second layer dye conjugate
1130—872 bp dsDNA target
1140—helper probes
FIG. 12
——— represents nucleic acid of the detection probe
B represents biotin coupled to a linker
x represents the number of nucleotides
y represents the number of hexaethyleneglycol phosphate monomers
FIG. 13
One-step nucleic acid dipstick assay detection of *Chlamydia trachomatis*
The numbers indicate the number of elementary bodies of *Chlamydia trachomatis*.
*NC: negative control
FIG. 14
Table: one-step nucleic acid dipstick assay detection of *Chlamydia trachomatis*

The invention claimed is:

1. A dipstick for testing for the presence of a target nucleic acid in a sample solution, wherein the dipstick comprises:
a chromatographic strip having a contact end for contacting the sample solution; and
a capture probe that is immobilized at a capture zone of the chromatographic strip remote from the contact end, wherein the capture probe comprises an oligonucleotide capable of hybridizing to the target nucleic acid or to a hook capture probe bound to the target nucleic acid, wherein the capture probe is linked to a capture probe spacer and the capture probe spacer is linked to the capture zone, thereby immobilizing the capture probe at the capture zone and spacing the capture probe from the capture zone, wherein:

i) the capture probe spacer is linked to one end of the capture probe, and the end of the capture probe that is not linked to the capture probe spacer is coupled to one or more nucleotides, which do not hybridize to the target nucleic acid when the capture probe is hybridized to the target nucleic acid or do not hybridize to the hook capture probe when the capture probe is hybridized to the hook capture probe;

ii) the capture probe spacer is linked to a part of the capture probe between the ends of the capture probe, and one or both ends of the capture probe are coupled to one or more nucleotides, which do not hybridize to the target nucleic acid when the capture probe is hybridized to the target nucleic acid or do not hybridize to the hook capture probe when the capture probe is hybridized to the hook capture probe;

iii) the capture probe spacer comprises a protein adsorbed directly to the capture zone, wherein the capture probe is covalently linked to the protein by a linker.

2. The dipstick of claim 1, further comprises a detection probe, that is releasably immobilized at a probe zone located between the contact end and the capture zone of the chromatographic strip such that sample solution passing the probe zone mobilizes the detection probe, wherein the detection probe is capable of hybridizing to the target nucleic acid to allow detection of the target nucleic acid.

3. The dipstick according to claim 2, wherein the detection probe is coupled to a label, which allows direct detection of the target nucleic acid when the detection probe is hybridized to the target nucleic acid.

4. The dipstick according to claim 2, wherein the detection probe is coupled to a detection ligand, which can be bound by a detection ligand binding moiety to allow indirect detection of the target nucleic acid when the detection probe is hybridized to the target nucleic acid.

5. The dipstick according to claim 4, wherein the label or detection ligand is linked to a detection probe spacer and the detection probe spacer is linked to the detection probe, thereby coupling the label or the detection ligand to the detection probe and spacing the label or the detection ligand from the detection probe.

6. A kit for testing for the presence of a target nucleic acid in a sample solution, wherein the kit comprises:

the dipstick of claim 1; and a detection probe capable of hybridizing to the target nucleic acid thereby allowing detection of the target nucleic acid utilizing the detection probe.

7. The kit according to claim 6, wherein the detection probe is coupled to a label allowing direct detection of the detection probe that is hybridized to the target nucleic acid, or a detection ligand allowing indirect detection of the detection probe that is hybridized to the target nucleic acid by a detection ligand binding moiety, wherein the label or the detection ligand is linked to a detection probe spacer and the detection probe spacer is linked to the detection probe thereby coupling the label or the detection ligand to the detection probe and spacing the label or the detection ligand from the detection probe.

* * * * *